United States Patent
Moszner et al.

(10) Patent No.: US 10,875,949 B2
(45) Date of Patent: Dec. 29, 2020

(54) POLYMERIZABLE MATERIALS BASED ON DIMERIZABLE BENZALDEHYDE DERIVATIVES

(71) Applicant: Ivoclar Vivadent AG, Schaan (LI)

(72) Inventors: Norbert Moszner, Triesen (LI); John Hendrik, Buchs (CH); Iris Lamparth, Grabs (CH); Christopher Barner-Kowollik, Kenmore (AU); Tim Krappitz, Red Hill (AU); Florian Feist, Auchenflower (AU)

(73) Assignee: Ivoclar Vivadent AG, Schaan (LI)

( * ) Notice: Subject to any disclaimer, the term of this patent is extended or adjusted under 35 U.S.C. 154(b) by 0 days.

(21) Appl. No.: 16/549,163

(22) Filed: Aug. 23, 2019

(65) Prior Publication Data
US 2020/0079888 A1 Mar. 12, 2020

(30) Foreign Application Priority Data

Sep. 11, 2018 (EP) .................................... 18193807
Sep. 21, 2018 (EP) .................................... 18196066

(51) Int. Cl.
| C08F 2/46 | (2006.01) |
| C08F 2/50 | (2006.01) |
| C08G 61/04 | (2006.01) |
| C08F 220/14 | (2006.01) |
| C08F 220/18 | (2006.01) |
| C08F 220/28 | (2006.01) |
| C07C 233/31 | (2006.01) |
| C07C 69/76 | (2006.01) |

(52) U.S. Cl.
CPC ............ C08F 220/14 (2013.01); C07C 69/76 (2013.01); C07C 233/31 (2013.01); C08F 220/18 (2013.01); C08F 220/28 (2013.01); *C08F 220/1804* (2020.02); *C08F 220/281* (2020.02); *C08F 2800/10* (2013.01)

(58) Field of Classification Search
CPC .... C07C 233/31; C08F 220/18; C08F 220/28; C08F 220/1811; C08F 220/14; C08F 220/36; C08F 220/1804; C08F 220/303; C08F 220/281; A61L 27/44; A61L 27/26; A61L 2430/12; A61L 2430/14; A61L 2430/06; A61L 2430/24; A61L 2430/16; C08L 33/10; C08L 33/12
USPC ................. 522/64, 6, 71, 189, 184, 1; 520/1
See application file for complete search history.

(56) References Cited

U.S. PATENT DOCUMENTS

| 2013/0274426 A1* | 10/2013 | Sugiura ................... A61K 6/887 526/123.1 |
| 2014/0073717 A1* | 3/2014 | Urban ................... C09D 133/06 522/121 |
| 2014/0323648 A1* | 10/2014 | Schmidt ................ C08F 220/36 524/558 |
| 2017/0007362 A1 | 1/2017 | Chen et al. |
| 2017/0166671 A1* | 6/2017 | Prenzel ....................... C08J 3/24 |

OTHER PUBLICATIONS

Pauloehrl, T. et al., "Adding Spatial Control to Click Chemistry: Phototriggered Diels-Alder Surface (Bio) functionaiization at Ambient Temperature," Angew. Chem. Int. Ed., 2012, 51, 1071-1074, Wiiey-VCH Verlag GmbH & Co. KGaA, Weinheim.
Claus, T. et al., "Simultaneous Dual Encoding of Three-Dimensional Structures by Light-Induced Modular Ligation," Angew. Chem. Int. Ed., 2016, 55, 3817-3822, Wiley-VCH Verlag GmbH & Co. KGaA, Weinheim.
Claus, T. et al., "Stepwise Light-Induced Dual Compaction of Single-Chain Nanoparticles," Macromolecular Rapid Communications, 2017, 38, 2017 Wiley-VCH Verlag GmbH & Co. KGaA, Weinheim.
Heinzmann, C. et al., "Supramolecular Polymer Networks Made by Solvent-Free Copolymerization of a Liquid 2-Ureido-4[1H]-pyrimidinone Methacrylamide," Macromolecules, American Chemical Society (ACS Publications), 2015, 8128-8136.
Heinenberg, M. et al., "Synthesis and modification of polymeric nitrones derived from polyrnerizable aldehydes," Macromol. Chem. Phys., 200, 1792-1805, 1999, Wiley-VCH Verlag GmbH, D-69451, Weinheim, 1999.

(Continued)

*Primary Examiner* — Jessica Whiteley
(74) *Attorney, Agent, or Firm* — Ann M. Knab; Thad McMurray

(57) ABSTRACT

The present invention relates to polymerizable and photochemically crosslinkable compositions which contain at least one polymerizable benzaldehyde derivative according to general formula I

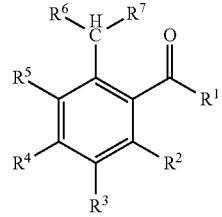

Formula I and which are suitable as materials for technical and medical applications, for example in surgery or ophthalmology, and in particular as dental materials.

13 Claims, No Drawings

(56) References Cited

OTHER PUBLICATIONS

Sandmann, B. et al., "Metal-Free Cycloaddition of Internal Alkynes and Multifunctional Azides Under Solvent-Free Conditions," Macromolecular Journals, Macromol. Chem. Phys. 2014, 215, 1603-1608, Wiley-VHC Verlag GmbH & Co. KGaA, Weinheim.
Oliver, W. C. et al., "An improved technique for determining hardness and elastic modulus using load and displacement sensing indentation experiments," J. Mater, Res., vol. 7, No. 6, pp. 1564-1583, Jun. 1992.

* cited by examiner

POLYMERIZABLE MATERIALS BASED ON DIMERIZABLE BENZALDEHYDE DERIVATIVES

CROSS-REFERENCE TO RELATED APPLICATIONS

This application claims priority to European patent application No. 18193807.7 filed on Sep. 11, 2018, and also claims priority to European patent application No. 18196066.7 filed on Sep. 21, 2018, both of the disclosures of which are incorporated herein by reference in their entirety.

TECHNICAL FIELD

The present invention relates to polymerizable and photochemically crosslinkable compositions based on benzaldehyde derivatives, which are suitable as materials for technical and medical applications, for example in surgery or ophthalmology, and in particular as dental materials.

BACKGROUND

Additive manufacturing processes, in which three-dimensional components are produced in layers from computer-aided design (CAD) data, have today gained currency in many technical fields and for the production of medical devices. These are processes such as e.g. stereolithography (SL), 3D printing, inkjet printing (IJP), 3D plotting, multijet modelling (MJM), solid freeform fabrication (SFF) or laser powder forming (LPF), with which models, components and shaped parts can be produced in a cost-effective manner. Such methods are also called generative processes.

Dental shaped parts are mostly constructed from a liquid and curable monomer or oligomer composition. Compositions used for this are, as a rule, based on mixtures of radically polymerizable (meth)acrylates or cationically polymerizable epoxy, vinyl ether or oxetane compositions. Di- or multifunctional monomers are mostly used here, and relatively brittle network polymers are formed. In addition to the polymerizable components, the materials often contain one or more fillers. The polymerizable components are also referred to as a matrix or resin.

In the dental industry, for the production of corrective splints for orthodontics, so-called aligners, a jaw/tooth model is first produced by means of additive manufacturing processes, by 3D printing. In order to obtain the corrective splints, a special deep-drawing film, which is based for example on polyurethane (PU), polyethylene terephthalate (PET) or polypropylene (PP), is then deep-drawn over this model. The model is then discarded. This is an indirect process for producing the corrective splints. The correction of the tooth position is effected in several steps. After the patient has had the first corrective splint applied, a new model of the altered tooth situation is manufactured in the described manner and the model is then discarded again. As up to 20 treatment stages are often necessary in order to achieve the desired tooth position, the treatment is associated with a substantial outlay on material.

Materials which can be processed directly by additive processes have not yet achieved the mechanical and biocompatible properties necessary for corrective splints. Known materials which yield approximately suitable mechanical properties have such a high viscosity that they can only be processed at high temperatures, and not at room temperature.

WO 2013/104486 A1 and corresponding U.S. 2014323648, which is hereby incorporated by reference, disclose adhesive and coating compositions which are cross-linkable by means of a photoinduced Diels-Alder or hetero-Diels-Alder reaction. The materials contain a component which has at least two dienophile double bonds and a second component with at least two diene-group-forming functionalities. At least one of these components must have more than two functionalities in order to bring about a crosslinking.

US 2017/0007362 A1, which is hereby incorporated by reference, describes crosslinked polymers which are to be suitable for orthodontic appliances and can be used in direct manufacturing processes. It furthermore discloses compositions polymerizable in a light-induced manner, from which the crosslinked polymers can be produced. The crosslinking is effected via multifunctional vinyl monomers, such as e.g. di(meth)acrylates or epoxy(meth)acrylates, or via the reaction of functional groups which have double bonds with thiols.

SUMMARY

The object of the invention is to provide materials which are suitable for stereolithographic processing and which in the cured state have mechanical properties which are suitable for medical-technical and for dental purposes, and in particular for corrective dental splints. Furthermore, the materials are to have a biocompatibility suitable for the named applications.

Moreover, after the curing the materials are to exhibit an as small as possible decrease in the restoring forces over an as long as possible period of time. A regression of at most 15% to 20% over a period of time of 14 days is sought.

In addition, after the curing the materials should have a high transparency and a weak inherent colouring, with the result that corrective splints can be produced which are as inconspicuous as possible. Moreover, the materials are to exhibit only a low water absorption.

DETAILED DESCRIPTION

The object is achieved according to the invention by compositions which contain at least one polymerizable compound according to general formula I,

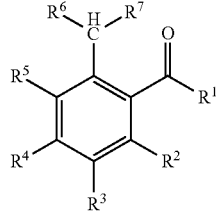

Formula I in which
$R^1$ is hydrogen, a branched or unbranched, saturated or unsaturated $C_1$-$C_{14}$ alkyl group which can be interrupted by O or S, a $C_6$-$C_{14}$ aryl group or a $C_4$-$C_{14}$ heteroaryl group which can contain N, O or S, wherein the alkyl, aryl or heteroaryl groups can be substituted with thioether, amino, alkoxy or alkyl groups with 1 to 14 carbon atoms or $C_6$-$C_{14}$ aryl groups and wherein the substituents can be bridged to each other, $R^{2-5}$ in each case independently of each other are hydrogen, an $NH_2$ group, a branched or unbranched, saturated or unsaturated thioether, amino, alkoxy or alkyl group with 1 to 14 carbon atoms, a branched or unbranched, saturated or unsaturated $C_7$-$C_{15}$ arylalkoxy group, preferably benzyloxy group (Ph-$CH_2$—O—), or a $C_6$-$C_{14}$ aryl group which can be bound via O or S, wherein $R^{2-5}$ can be bridged to each other and $R^2$ and/or $R^4$ is/are —X—SP-PG, X is dispensed with or is —O—, —CO—O— or —O—CO—, SP is a linear or branched $C_1$-$C_6$ alkylene group, wherein the alkylene group can be interrupted by O, S, —CO—O—, —O—CO— and/or phenylene (Ph), PG is a polymerizable group, $R^{6-7}$ in each case independently of each other are hydrogen or a $C_1$-$C_{10}$ alkyl group which can be branched or unbranched, saturated or unsaturated.

The polymerizable group (PG) is preferably a radically or cationically polymerizable group, particularly preferably a radically polymerizable group.

Preferred radically polymerizable groups (rPG) are vinyl, (meth)acrylate (—O—C(=O)—C($R^8$)=$CH_2$ where $R^8$=H or —$CH_3$) or (meth)acrylamide (—N($R^9$)—C(=O)—C($R^{10}$)=$CH_2$ where $R^9$=H or $C_1$-$C_4$ alkyl and $R^{10}$=H or —$CH_3$) groups, particularly preferably (meth)acrylate groups.

Preferred cationically polymerizable groups (cPG) are epoxy, oxetane or vinyl ether groups, particularly preferably epoxy groups.

Compounds in which $R^1$ is hydrogen or a $C_1$-$C_4$ alkyl group, $R^{2-5}$ in each case independently of each other are hydrogen or a $C_1$-$C_4$ alkoxy or $C_1$-$C_4$ alkyl group, wherein $R^2$ and/or $R^4$ is/are —X—SP-PG, X is —O—, SP is a linear $C_2$-$C_6$ alkylene group, wherein the alkylene group can be interrupted by O, —CO—O— and/or phenylene (Ph), preferably is a $C_2$-$C_4$ alkylene group or —$CH_2$-Ph-CO—O—$CH_2CH_2$—, PG is a cationically or preferably radically polymerizable group, in particular is a (meth)acrylate group or an acrylamide group, $R^{6-7}$ are both hydrogen or $R^6$=$C_1$-$C_{10}$ alkyl and $R^7$=H are preferred.

Compounds in which $R^1$ is hydrogen or —$CH_3$, $R^{2-5}$ in each case independently of each other are hydrogen, —$CH_3$ or —$OCH_3$, wherein $R^2$ or $R^4$ is —X—SP-PG, X is —O—, SP is a linear $C_2$-$C_6$ alkylene group, wherein the alkylene group can be interrupted by O, —CO—O— and/or phenylene (Ph), preferably is a $C_2$-$C_4$ alkylene group or —$CH_2$-Ph-CO—O—$CH_2CH_2$—, PG is a cationically or preferably radically polymerizable group, in particular is a (meth)acrylate group or an acrylamide group, $R^{6-7}$ in each case are hydrogen are particularly preferred.

Compounds in which $R^1$ is hydrogen, $R^{2-5}$ in each case independently of each other are hydrogen or —$CH_3$, wherein $R^2$ or $R^4$ is —X—SP-PG, X is —O—, SP is a linear $C_2$-$C_4$ alkylene group, wherein the alkylene group can be interrupted by O, —CO—O— and/or phenylene (Ph), preferably is a $C_2$ alkylene group or —$CH_2$-Ph-CO—O—$CH_2CH_2$—, PG is a radically polymerizable group, in particular a (meth)acrylate group or an acrylamide group, $R^{6-7}$ in each case are hydrogen are quite particularly preferred.

In addition to the compound of Formula I, the compositions according to the invention preferably contain no further 1,3-dienes and no dienophiles, which undergo cycloaddition reactions.

Formula I extends only to those compounds which are compatible with the theory of chemical valence. The indication that a radical is interrupted e.g. by one or more O atoms is to be understood to mean that these atoms are inserted in each case into the carbon chain of the radical. These atoms are thus bordered on both sides by C atoms and cannot be terminal. $C_1$ radicals cannot be interrupted.

The benzaldehyde derivatives according to the invention of general formula I are accessible in a manner known per se and can be produced according to known synthesis methods. According to a preferred synthesis route, e.g. polymerizable o-methylbenzaldehyde derivatives (P-MBA), which bear a bound polymerizable group (PG) via a spacer (SP), are produced starting from 2,3-dimethylanisole (DMA) via 2-methoxy-5-methyl-benzaldehyde (MMBA) and 2-hydroxy-5-methyl-benzaldehyde (HMBA):

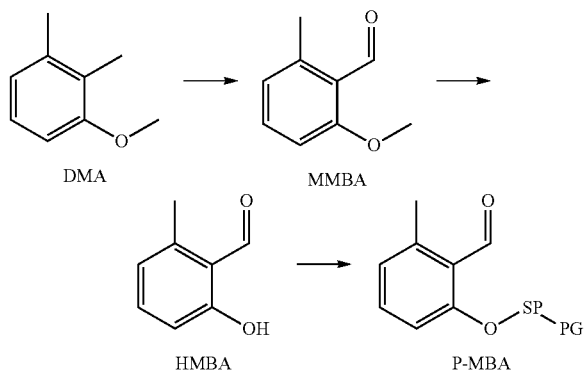

The particularly preferred 4-[(2-formyl-3-methylphenoxy)-methyl]-benzoic acid-(2-methacryloyloxyethyl)-ester (PEMA) can preferably be produced from the commercially available 2,3-dimethylanisole. Here, the oxidation to 2-methoxy-6-methylbenzaldehyde in the presence of potassium peroxodisulphate is effected first and then the separation of the methoxy group in the presence of aluminium chloride. Subsequently, the 2-hydroxy-6-methylbenzaldehyde obtained is reacted with 4-(bromomethyl)benzoic acid methyl ester and the ester is saponified. The 4-[(2-formyl-3-methylphenoxy)-methyl]-benzoic acid released is finally esterified to PEMA with hydroxyethyl methacrylate (Pauloehrl et al., Angew. Chem. Int. Ed. Engl. 51 (2012) 1071-1074; Klaus et al., Angew. Chem. Int. Ed. Engl. 55 (2016) 3817-3822):

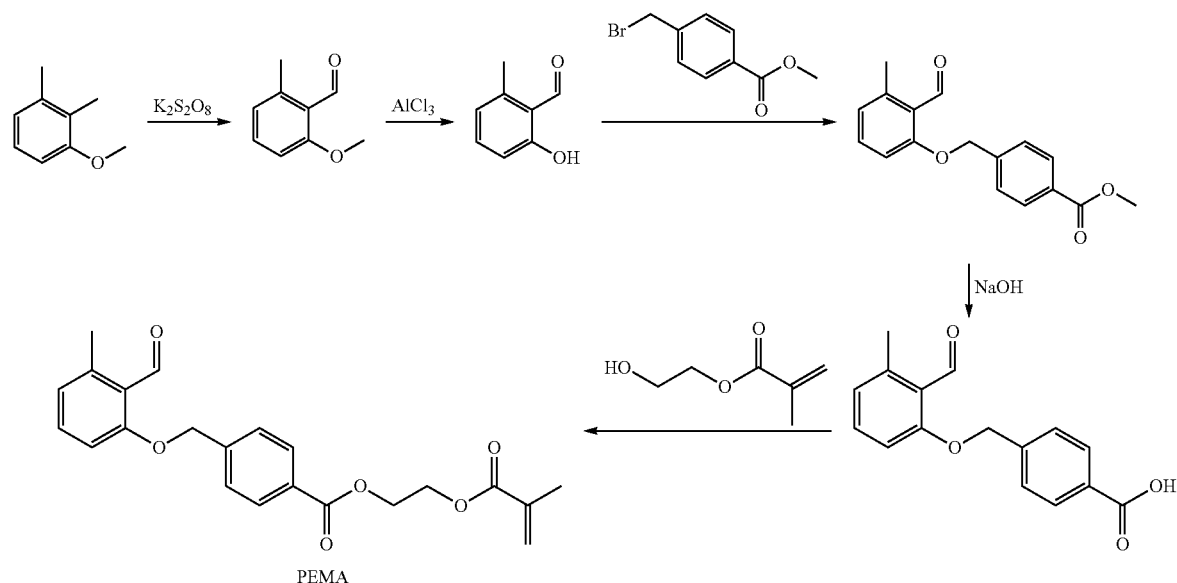
Preferred benzaldehyde derivatives of general formula I are:
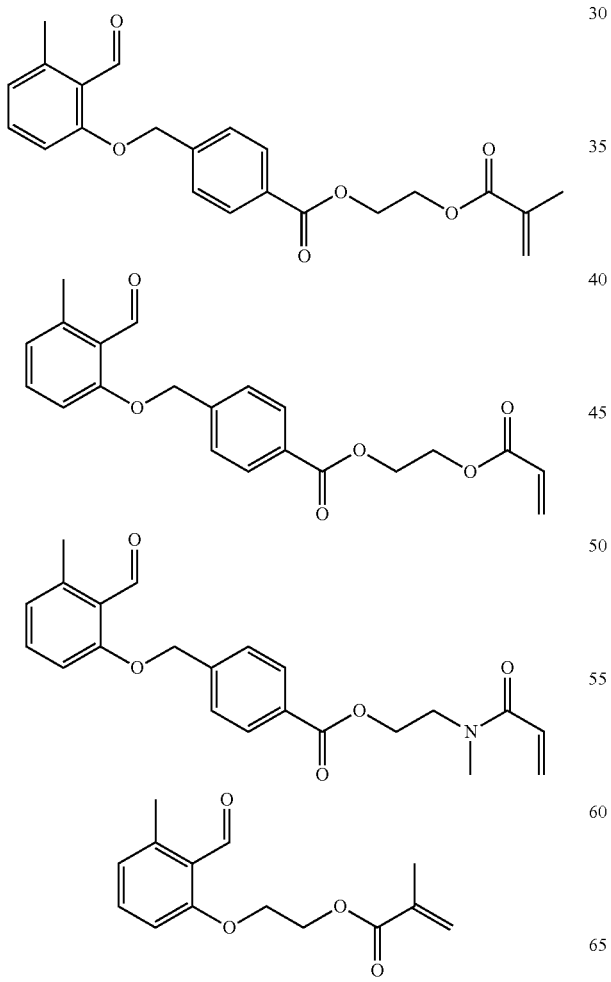
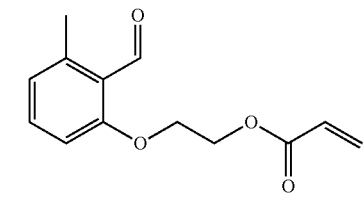
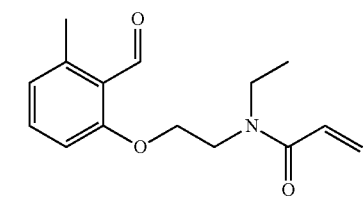
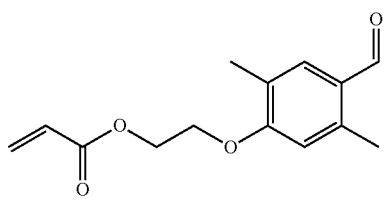
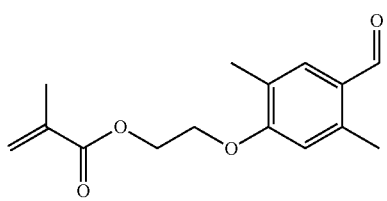

A particularly preferred benzaldehyde derivative of general formula I is:

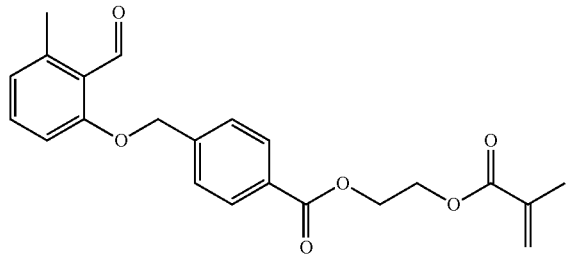

The benzaldehyde derivatives according to the invention can be photochemically crosslinked during or after the polymerization. For this, they are irradiated with UV-A light, which brings about a dimerization of the benzaldehyde derivatives by means of a cycloaddition reaction.

The benzaldehyde derivatives according to the invention can be used directly, i.e. in monomeric form, or as a resin component, in oligomeric or polymeric form. Oligomeric or polymeric forms can be produced using known methods by radical or cationic bulk or solution homo- or copolymerization of the benzaldehyde derivatives. The monomeric form of the polymerizable benzaldehyde derivatives is preferred.

The monomeric, oligomeric and/or polymeric benzaldehyde derivatives can be used as materials for the production of shaped bodies by additive processes.

In addition to the benzaldehyde derivatives according to the invention of Formula I, the compositions preferably contain one or more polymerizable comonomers, wherein 1,3-dienes and dienophiles, which can undergo cycloaddition reactions, are preferably ruled out as comonomers. Preferred comonomers are cationically or preferably radically polymerizable monomers.

As dental materials, in particular for the production of dental braces or splints for correcting malocclusions, materials which contain at least one mono- or multifunctional (meth)acrylate as radically polymerizable monomer are preferred. By monofunctional (meth)acrylates is meant compounds with one, by multifunctional (meth)acrylates is meant compounds with two or more, preferably 2 to 4, radically polymerizable groups. The mono- or multifunctional (meth)acrylates can contain further functional groups, such as e.g. hydroxy, ester, silyl or ureido groups. The flexibility and the properties of the cured materials can be influenced in a targeted manner via the structure of the radically polymerizable (meth)acrylate comonomers.

Preferred monofunctional (meth)acrylates are methyl, ethyl, n-propyl, n-butyl, 2-ethylhexyl, cyclohexyl, benzyl, tetrahydrofurfuryl, isobornyl or lauryl (meth)acrylate as well as p-cumyl-phenoxyethyleneglycol (meth)acrylate or 2-(2-biphenyloxy)-ethyl (meth)acrylate and mixtures thereof. Particularly preferred monofunctional (meth)acrylates are methyl acrylate (MA), ethyl acrylate (EA), methyl methacrylate (MMA), butyl methacrylate (BMA), tetrahydrofurfuryl methacrylate (THFMA), isobornyl methacrylate (IBOMA) and mixtures thereof. Methyl acrylate (MA), methyl methacrylate (MMA), butyl methacrylate (BMA), tetrahydrofurfuryl methacrylate (THFMA), isobornyl methacrylate (IBOMA) and mixtures thereof are quite particularly preferred.

Preferred monofunctional (meth)acrylates with additional functional groups are hydroxyalkyl, alkyloxycarbonylalkyl, silyl and ureido (meth)acrylates, such as e.g. 2-hydroxyethyl, 2-hydroxypropyl, 2-acetoxyethyl, 3-trimethylsilylpropyl and 2-ureido-4-[1H]-pyrimidone (meth)acrylate, as well as acid-group-containing (meth)acrylates, such as e.g. (meth)acrylic acid, 2-(hydroxymethyl) acrylic acid, 4-(meth)acryloyloxyethyltrimellitic acid, 10-methacryloyloxydecylmalonic acid, 2-methacryl-oyloxyethylphosphonic acid, or 2-[4-(dihydroxyphosphoryl)-2-oxa-butyl]-acrylic acid, and mixtures thereof. Particularly preferred monofunctional (meth)acrylates with additional functional groups are 2-hydroxyethyl and 2-hydroxypropyl (meth)acrylate, 2-ureido-4-[1H]-pyrimidone (meth)acrylate and mixtures thereof. A quite particularly preferred monofunctional (meth)acrylate with additional functional groups is 2-ureido-4-[1H]-pyrimidone (meth)acrylate.

Preferred multifunctional (meth)acrylates are bisphenol A di(meth)acrylate, such as e.g. 2,2-bis[4-(2-hydroxy-3-(meth)acryl-oyloxypropyl)phenyl]propane (bis-G(M)A; an addition product of (meth)acrylic acid and bisphenol A diglycidylether), ethoxylated or propoxylated bisphenol A di(meth)acrylate, such as e.g. 2-[4-(2-methacryloyloxyethoxyethoxy)phenyl]-2-[4-(2-methacryloyloxyethoxy)phenyl]-propane) (SR-348c, from Sartomer; contains 3 ethoxy groups), 2,2-bis[4-(2-(meth)-acryloxypropoxy)phenyl]propane, 1,6-bis-[2-(meth)acryl-oyloxyethoxycarbonylamino]-2,2,4-trimethylhexane (UD(M)A; an addition product of 2-hydroxyethyl (meth)acrylate and 2,2,4-trimethylhexamethylene diisocyanate), di-, tri- or tetraethylene glycol di(meth)acrylate, trimethylolpropane tri(meth)acrylate, pentaerythritol tetra(meth)acrylate, glycerol di- and tri(meth)acrylate, 1,4-butanediol di(meth)acrylate, 1,10-decanediol di(meth)acrylate ($D_3(M)A$), 1,12-dodecanediol di(meth)acrylate and mixtures thereof. Particularly preferred multifunctional (meth)acrylates are di-, tri- or tetraethyleneglycol di(meth)acrylate, glycerol di- and tri(meth)acrylate, 1,4-butanediol di(meth)acrylate, 1,10-decanediol di(meth)acrylate ($D_3(M)A$), 1,12-dodecanediol di(meth)acrylate and mixtures thereof. Quite particularly preferred multifunctional (meth)acrylates are di-, tri- or tetraethyleneglycol di(meth)acrylate, 1,4-butanediol di(meth)-acrylate, 1,10-decanediol di(meth)acrylate ($D_3(M)A$) and mixtures thereof.

Preferred (meth)acrylamides are liquid tertiary acrylamides, such as e.g. N,N-dimethylacrylamide, N,N-diethylacrylamide, N,N-diisopropylacrylamide, N-(2-hydroxyethyl)-N-methyl-acrylamide or N,N'-diethyl-1,3-bis(acrylamido)-propane, liquid secondary methacrylamides, such as e.g. 2-ureido-4[1H]-pyrimidone methacrylamide (UPyMAA), and mixtures thereof. Particularly preferred (meth)acrylamides are N,N-dimethylacrylamide, N,N-diethylacrylamide, N,N'-diethyl-1,3-bis(acrylamido)-propane, 2-ureido-4[1H]-pyrimidone methacrylamide (UPyMAA) and mixtures thereof. Quite particularly preferred (meth)acrylamides are N,N-dimethylacrylamide, N,N-diethylacrylamide, 2-ureido-4[1H]-pyrimidone methacrylamide (UPyMAA) and mixtures thereof.

Preferred cationic polymerizable monomers are monomers that are polymerizable in a cationically ring-opening manner, in particular glycidyl ether, cycloaliphatic epoxides and oxetanes, such as e.g. phenylglycidyl, benzylglycidyl or bisphenol A diglycidyl ether, cyclohexene oxide, 3,4-epoxycyclohexylmethyl-3,4-epoxycyclohexane carboxylate, bis (3,4-epoxycyclohexylmethyl)adipate, vinylcyclohexene dioxide, 3-ethyl-3-hydroxymethyloxetane, 1,10-decanediyl-bis-(oxymethylene)-bis-(3-ethyloxetane) or 3,3-(4-xylylenedioxy)-bis-(methyl-3-ethyloxetane) and mixtures thereof. Particularly preferred cationically polymerizable monomers are 3,4-epoxy-cyclohexylmethyl-3,4-epoxycyclohexane carboxylate, bis(3,4-epoxycyclohexylmethyl)adipate, 3-ethyl-3-hydroxymethyloxetane, 1,10-decanediyl-bis-(oxymethylene)-bis-(3-ethyloxetane) and mixtures thereof. Quite particularly preferred cationically polymerizable monomers are 3,4-epoxy-cyclohexylmethyl-3,4-epoxy-cyclohexane carboxylate, 3-ethyl-3-hydroxymethyloxetane and mixtures thereof.

The compositions according to the invention can be cured either in one stage or in two stages. The curing is preferably effected during the stereolithographic processing of the materials. The one-stage curing is preferably effected by UV-A light, particularly preferably with a wavelength in the range of from 320 to 380 nm. For this, the compositions preferably additionally contain a UV-A photoinitiator.

The polymerization of the benzaldehyde derivatives according to the invention of Formula I with the optionally present comonomers is initiated by the irradiation with UV-A light. At the same time a crosslinking of the material is brought about by the UV-A irradiation.

The crosslinking is effected via the benzaldehyde derivatives according to the invention. The irradiation e.g. of the o-methylbenzaldehyde MMBA with UV-A light leads to the intermediate formation of an enol, an o-quinodimethane derivative (5,6-bis(methylene)-1,3-cyclohexadiene derivative), which can react with an electron-poor dienophile, e.g. maleimide or fumaric acid ester, to form a corresponding Diels-Alder adduct. If there is no suitable dienophile, two o-quinodimethane groups can dimerize in a cycloaddition and thus bring about a crosslinking of two polymer chains:

according to the invention is that the degree of crosslinking, and thus the flexibility of the polymer networks, can be adjusted in a targeted manner by the duration of the irradiation.

The crosslinking density of the polymer networks can here be controlled during and after the processing by the irradiation duration. In this way, with a given starting composition, materials with different degrees of crosslinking, and thus with different mechanical properties, can be obtained. In contrast, when multifunctional (meth)acrylates are used as crosslinkers the crosslinking density is predetermined by the proportion thereof in the composition, with the result that a different composition must be provided in each case for different crosslinking densities. The combination of benzaldehyde derivatives according to the invention and multifunctional (meth)acrylates makes a basic crosslinking possible via the proportion of multifunctional (meth)acrylates, which can be varied in a targeted manner by the photoinduced dimerization of the benzaldehyde derivatives. In combinations of benzaldehyde derivatives according to the invention and multifunctional (meth)acrylates the proportion of multifunctional (meth)acrylates should be preferably not greater than 20 wt.-%, particularly preferably not greater than 15 wt.-% and quite particularly preferably not greater than 10 wt.-%, in each case relative to the total mass of the composition.

Moreover, a further advantage of the benzaldehyde derivatives according to the invention is that the crosslinking density of the polymer networks can be varied locally in the product by the irradiation, with the result that products with different degrees of crosslinking can be produced in different Dimerization

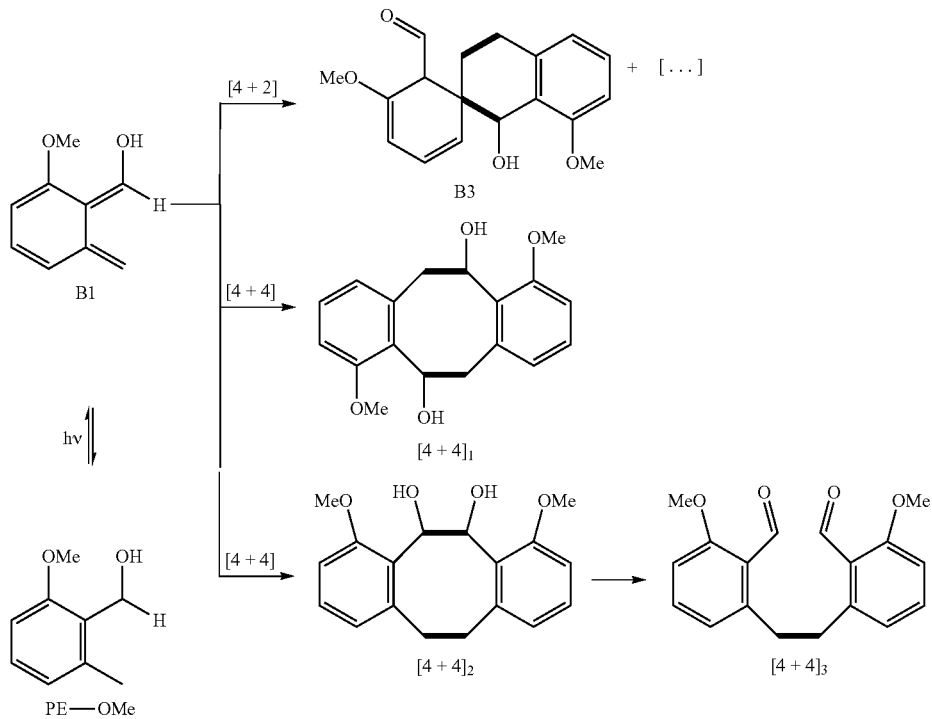

It has been found that this reaction can be used advantageously for the production of shaped bodies by additive processes. An advantage of the benzaldehyde derivatives areas of the product. Furthermore, the crosslinking can also be effected only at the end of the completion of the shaped parts.

For the two-stage curing, a photoinitiator for the visible range, a thermal initiator or a redox initiator is additionally added to the compositions. In the case of irradiation with visible light or if a thermal initiator or redox initiator is used, a radical or cationic polymerization of the benzaldehyde derivatives and the optionally present comonomers initially takes place in the first stage. In the second stage an irradiation with UV-A light is effected, which leads to the crosslinking of the polymer chains formed in the first stage by dimerization of the benzaldehyde derivative groups present in the chains.

The network structure and the properties of the network polymers formed can be controlled via the content of benzaldehyde derivatives according to the invention of Formula I as well as the irradiation duration. The maximum crosslinking density increases with the content of benzaldehyde derivatives according to the invention of Formula I, wherein the crosslinking density can be controlled in the individual case via the irradiation duration with UV-A light. A longer irradiation duration brings about a higher degree of dimerization and thus a higher degree of crosslinking.

Preferred photoinitiators for the UV-A range (320 to 380 nm) are benzophenone, benzoin, 2,2-dimethoxy-1,2-diphenylethan-1-one (Irgacure® 651), 1-hydroxycyclohexylphenylketone (Irgacure® 184), 2-hydroxy-2-methyl-1-phenyl-propanone (Irgacure® 1173) as well as acyl and bisacyl phosphine oxides, such as e.g. the commercially obtainable compounds 2,4,6-trimethylbenzoyldiphenyl phosphine oxide (Lucerin® TPO), ethyl-(2,4,6-trimethylbenzoyl)phenyl phosphinate (Irgacure® TPO-L) and bis(2,4,6-tri-methylbenzoyl)phenyl phosphine oxide (Irgacure® 819), and mixtures thereof. Camphorquinone (CQ), 2,2-dimethoxy-2-phenyl-acetophenone, bis(2,4,6-trimethylbenzoyl)phenyl phosphine oxide (Irgacure® 819) 2,4,6-trimethylbenzoyldiphenyl phosphine oxide (Lucerin® TPO), ethyl-(2,4,6-trimethylbenzoyl)phenyl phosphinate (Irgacure® TPO-L) and mixtures thereof are particularly preferred.

Preferred photoinitiators for the visible range (380 to 780 nm) are α-diketones or derivatives thereof, such as 9,10-phenanthrene quinone, 1-phenyl-propane-1,2-dione, diacetyl or 4,4'-dichlorobenzil. Combinations of α-diketones with amines are also preferably suitable as reducing agents, such as e.g. 4-(dimethylamino)-benzoic acid ester (EDMAB), N,N-dimethylaminoethyl methacrylate, N,N-dimethyl-sym.-xylidine or triethanolamine. Suitable Norrish type-I photoinitiators for the visible range are monoacyltrialkyl-, diacyldialkyl- or tetraacylgermanium compounds as well as tetraacylstannanes, such as e.g. benzoyltrimethylgermane, dibenzoyl diethyl germane, bis(4-methoxybenzoyl)diethylgermane (MBDEGe), tetrakis(2-methylbenzoyl)germane or tetrakis(mesitoyl)stannane. Bis(4-methoxybenzoyl)diethylgermane (MBDEGe) is particularly preferred.

Moreover, mixtures of the named photoinitiators with amines as accelerators can preferably also be used as initiators for the visible range. The combination of camphorquinone (CQ) and 4-dimethylaminobenzoic acid ethyl ester (EDMAB) is particularly preferred.

Preferred photoinitiators for the cationic polymerization are aromatic diaryliodonium or triarylsulphonium salts, e.g. the commercially available compounds 4-octyloxyphenyl-phenyl-iodonium hexafluoro antimonate or phosphate, isopropylphenyl-methylphenyl-iodonium tetrakis(pentafluorophenyl)borate or triarylsulphonium hexafluoro antimonate (CYRACURE® UVI 6976). 4-Octyloxyphenyl-phenyl-iodonium hexafluoro antimonate or phosphate and isopropylphenyl-methylphenyl-iodonium tetrakis-(pentafluorophenyl)borate are particularly preferred. These are active in the wavelength range of from 320 to 400 nm.

Preferred thermal initiators for the radical polymerization are azo compounds, such as e.g. 2,2'-azobis(isobutyronitrile) (AIBN) or azobis-(4-cyanovaleric acid), peroxides, such as e.g. dibenzoylperoxide, dilauroylperoxide, tert-butylperoctoate, tert-butylperbenzoate or di-(tert-butyl)-peroxide, redox initiator combinations, such as e.g. combinations of benzoylperoxide with amines, such as e.g. N,N-dimethyl-p-toluidine, N,N-dihydroxyethyl-p-toluidine, p-dimethylaminobenzoic acid ethyl ester or N,N-dimethyl-sym.-xylidine, combinations of inorganic peroxides, such as e.g. potassium and ammonium peroxodisulphate, with reducing agents, such as e.g. sulphite, hydrogen sulphite, thiosulphate, sulphinic acids, amines, endiols or Fe(II) salts, or redox systems consisting of organic peroxides or hydroperoxides and reducing agents, such as e.g. ascorbic acid, barbiturates, thioureas or sulphinic acids. The compositions according to the invention can preferably contain one or more thermal initiators.

Compounds of transition metals which have at least two stable valence states are preferred as redox initiators. These are, above all, compounds of the elements copper, iron, vanadium, nickel or cobalt, wherein copper compounds are particularly preferred and these are preferably used as very organosoluble compounds, such as e.g. as acetyl acetonate, naphthenate or 2-ethyl-hexanoate.

The compositions according to the invention furthermore preferably contain one or more organic or preferably inorganic fillers, wherein particulate fillers are preferred. Preferred inorganic particulate fillers are oxides, such as $SiO_2$, $ZrO_2$ and $TiO_2$ or mixed oxides of $SiO_2$, $ZrO_2$, $ZnO$ and/or $TiO_2$ with a particle size of from 0.005 to 1.0 μm, nanoparticulate or microfine fillers with a particle size of from 5 to 300 nm, such as pyrogenic silica or precipitated silica, and X-ray-opaque fillers, such as ytterbium trifluoride, tantalum (V) oxide, barium sulphate or mixed oxides of $SiO_2$ with ytterbium(III) oxide or tantalum(V) oxide, with a particle size of from 0.2 to 5 μm.

Unless otherwise stated, all particle sizes are weight-average particle sizes, for which the particle-size determination is effected by means of static light scattering, preferably using a static laser scattering particle size analyser LA-960 (Horiba, Japan). Here, a laser diode with a wavelength of 655 nm and an LED with a wavelength of 405 nm are used as light sources in a measurement range of from 0.1 to 1000 μm. The use of two light sources with different wavelengths makes it possible to measure the entire particle-size distribution of a sample in only one measurement pass, wherein the measurement is carried out as a wet measurement. For this, a 0.1 to 0.5% aqueous dispersion of the filler is produced and the scattered light thereof is measured in a flow cell. The scattered-light analysis for calculating particle size and particle-size distribution is effected in accordance with the Mie theory according to DIN/ISO 13320.

The measurement of the particle size in the range of from 5 nm to 0.1 μm is preferably effected by dynamic light scattering (DLS) of aqueous particle dispersions with an ALV/CGS-3 Compact Goniometer (ALV-Laser Vertriebsgesellschaft, Langen, Germany) with a He—Ne laser with a wavelength of 633 nm, at a scattering angle of 90° at 25° C.

Fillers are divided, according to particle size, into macrofillers and microfillers. Macrofillers are obtained e.g. by grinding quartz, X-ray-opaque glasses, borosilicates or ceramic, are preferably of a purely inorganic nature and mostly consist of splinter-like parts, which often have an average particle size of from 0.3 to 15 μm. Pyrogenic $SiO_2$ or precipitated silica, or also mixed oxides, e.g. $SiO_2$—$ZrO_2$, which are available by hydrolytic co-condensation of metal alkoxides, are preferably used as microfillers. The microfillers preferably have an average particle size of from 5 to 100 nm. Fillers with a small particle size have a greater thickening action.

The fillers are preferably surface-modified, particularly preferably by silanization, quite particularly preferably by radically polymerizable silanes, in particular with 3-methacryloyloxypropyltrimethoxysilane. For the surface-modification of non-silicate fillers, e.g. of $ZrO_2$ or $TiO_2$, functionalized acidic phosphates, such as e.g. 10-methacryloyloxydecyl dihydrogen phosphate can also be used.

The compositions according to the invention can advantageously contain further additives, above all stabilizers, colorants, optical brighteners, plasticizers or UV absorbers.

The materials according to the invention preferably contain the following components:
a) 0.1 to 50 wt.-%, preferably 1 to 40 wt.-% and particularly preferably 1 to 20 wt.-% of at least one benzaldehyde derivative of Formula I,
b) 30 to 99 wt.-%, preferably 40 to 95 wt.-% and particularly preferably 50 to 95 wt.-% of at least one further monofunctional radically or cationically polymerizable monomer,
c) 0 to 20 wt.-%, preferably 0 to 15 wt.-% and particularly preferably 0 to 10 wt.-% of at least one multifunctional radically or cationically polymerizable monomer,
d) 0.001 to 5.0 wt.-%, preferably 0.01 to 3.0 wt.-% and particularly preferably 0.1 to 1.0 wt.-% of at least one initiator, in particular photoinitiator,
e) 0 to 5.0 wt.-%, preferably 0 to 3.0 wt.-% and particularly preferably 0 to 1.5 wt.-% additive(s).

The materials according to the invention for additive processes preferably contain the following components:
a) particularly preferably 5.0 to 20 wt.-% of at least one benzaldehyde derivative of Formula I,
b) particularly preferably 40 to 94 wt.-% of at least one further monofunctional radically or cationically polymerizable monomer,
c) particularly preferably 0 to 10 wt.-% of at least one multifunctional radically or cationically polymerizable monomer,
d) 0.1 to 1.0 wt.-% of at least one initiator, in particular photoinitiator,
e) particularly preferably 0 to 3.0 wt.-% additive(s),
f) particularly preferably 0 to 40 wt.-% filler(s).

The materials according to the invention for medical devices preferably contain the following components:
a) particularly preferably 3.0 to 10 wt.-% of at least one benzaldehyde derivative of Formula I,
b) particularly preferably 40 to 95 wt.-% of at least one further monofunctional radically or cationically polymerizable monomer,
c) particularly preferably 0 to 15 wt.-% of at least one multifunctional radically or cationically polymerizable monomer,
d) 0.1 to 1.0 wt.-% of at least one initiator, in particular photoinitiator,
e) particularly preferably 0.1 to 3.0 wt.-% additive(s).

Moreover, the compositions according to the invention can contain one or more fillers. Compositions which contain 0 to 50 wt.-%, particularly preferably 0 to 40 wt.-% and quite particularly preferably 0 to 20 wt.-% of at least one filler are preferred. Compositions without fillers are particularly preferred.

Unless stated otherwise, all the percentages here are in percent by weight and relate to the total mass of the material.

Compositions which consist of the named substances are particularly preferred. Furthermore, those compositions in which the individual components are in each case selected from the above-named preferred and particularly preferred substances are preferred.

The compositions according to the invention can be processed by stereolithographic processes. It has surprisingly been found that, after the curing and crosslinking, materials according to the invention which contain benzaldehyde derivatives of Formula I have comparable mechanical properties to known deep-drawing films based on polyurethanes. Typical values for such films are an elastic modulus $E_{red}$ of from 0.5 to 2.0 GPa and a hardness of from 30 to 80 MPa. After polymerization and crosslinking, the materials according to the invention have a comparable reduced elastic modulus $E_r$ and a comparable hardness. The materials according to the invention preferably have a reduced elastic modulus $E_r$ of from 0.30 to 7.00 GPa, particularly preferably 0.70 to 6.00 GPa and quite particularly preferably of from 0.90 to 5.80 GPa, and a hardness of from 30 to 500 MPa, particularly preferably 40 to 400 MPa and quite particularly preferably 50 to 350 MPa.

The mechanical properties (reduced elastic modulus $E_r$ and hardness) of the cured samples are preferably determined by means of nanoindentation (instrumented penetration test) using a Hysitron TL950 nanoindenter (Bruker). The load-controlled measurements with a Berkovich tip are carried out at a maximum loading force of 2000 µN with a loading time of 1 s, a loading segment of 2 s as well as an unloading of 1 s. The analysis is effected using the Oliver-Pharr method (W. C. Oliver, G. M. Pharr, J. Mater In: Res. 7, 1992, p. 1564). Using measurement methods analogous to B. Sandmann, B. Happ, J. Vitz, R. M. Paulus, M. D. Hager, P. Burtscher, N. Moszner, U. S. Schubert, Macromol. Chem. Phys. 2014, 215, 1603, measurements are performed which yield comparable elastic modulus values for dimethacrylate photopolymers e.g. from the bending test.

The materials according to the invention are particularly suitable for the production of shaped bodies for dental, but also for non-dental, purposes e.g. by casting, pressing and in particular by additive processes such as 3D printing.

The materials according to the invention are furthermore suitable as medical-technical materials for surgery, such as e.g. as materials for the production of medical devices such as implants for auditory prostheses, cartilage or bone replacement parts, and for ophthalmology, such as e.g. as materials for the production of intraocular lenses, which are used e.g. as artificial lenses for the eye after removal of the natural lens in the case of cataract surgery, and in particular for the production of dental prostheses and appliances for orthodontics. The materials according to the invention are quite particularly suitable as dental materials for the production of appliances for orthodontics such as dental braces or splints, or templates for correcting malocclusions, in particular by additive processes.

The invention moreover relates to the use of benzaldehydes of Formula I for the production of medical-technical materials, in particular dental materials.

The invention is explained in further detail in the following with reference to examples.

EMBODIMENT EXAMPLES

Example 1

4-[(2-Formyl-3-methylphenoxy)-methyl]-benzoic acid-(2-methacryloyloxyethyl)-ester (PEMA)

1st Stage: 2-methoxy-6-methylbenzaldehyde (MMBA)

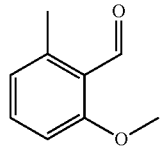

A solution of 2,3-dimethylanisole (10.00 g, 73.4 mmol) in acetonitrile (500 ml) was added to a mixture of copper(II) sulphate pentahydrate (18.14 g, 72.7 mmol) and potassium peroxodisulphate (59.81 g, 0.22 mol) in water (700 ml) and heated for 30 min at reflux. After cooling, water (100 ml) and dichloromethane (150 ml) were added and the phases were separated. The aqueous phase was extracted with dichloromethane (2×200 ml). The combined organic phases were dried over anhydrous sodium sulphate, filtered and concentrated on a rotary evaporator. 4:1 n-heptane/ethyl acetate (200 ml) was added to the brown oil and this was filtered over silica gel. The filtrate was concentrated on a rotary evaporator. 4.63 g (30.8 mmol; 42%) of a gradually crystallizing yellowish oil was obtained.

$^1$H-NMR (CDCl$_3$, 400 MHz): δ=10.63 (s, 1H; HC=O), 7.37 (t, 1H; J=8.0 Hz; Ar—H), 6.80 (m, 2H; Ar—H), 3.88 (s, 3H; O—CH$_3$), 2.56 (s, 3H; Ar—CH$_3$).

$^{13}$C-NMR (CDCl$_3$, 100.6 MHz): δ=192.2 (C=O), 163.0 (Ar—C), 141.9 (Ar—C), 134.4 (Ar—CH), 123.9 (Ar—CH), 123.1 (Ar—C), 108.9 (Ar—CH), 55.6 (O—CH$_3$), 21.4 (CH$_3$).

2nd Stage: 2-hydroxy-6-methylbenzaldehyde (HMBA)

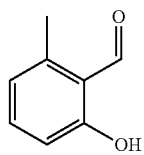

Anhydrous aluminium chloride (24.44 g, 0.183 mol) was added carefully to a solution of 2-methoxy-6-methylbenzaldehyde (18.35 g, 0.122 mol) in dichloromethane (150 ml) and the initially vigorously foaming reaction mixture was stirred at ambient temperature. After 2 h water (100 ml) was added dropwise, accompanied by ice cooling, and the phases were separated. The aqueous phase was extracted with dichloromethane (2×50 ml). The combined organic phases were washed with saturated aqueous sodium chloride solution (100 ml), dried over anhydrous sodium sulphate and filtered over silica gel. The filtrate was concentrated on a rotary evaporator. 14.9 g (0.110 mol; 90%) of a yellowish oil was obtained.

$^1$H-NMR (CDCl$_3$, 400 MHz): δ=11.90 (s, 1H; OH), 10.27 (s, 1H; HC=O), 7.34 (t, 1H; J=8.0 Hz; Ar—H), 6.78 (d, 1H; J=8.5 Hz, Ar—H), 6.68 (m, 1H; Ar—H), 2.56 (s, 3H; Ar—CH$_3$).

$^{13}$C-NMR (CDCl$_3$, 100.6 MHz): δ=195.2 (C=O), 163.0 (Ar—C), 142.0 (Ar—C), 137.2 (Ar—CH), 121.6 (Ar—CH), 118.3 (Ar—C), 115.9 (Ar—CH), 17.9 (CH$_3$).

3rd Stage: 4-[(2-formyl-3-methylphenoxy)-methyl]-benzoic acid methyl ester (FPBM)

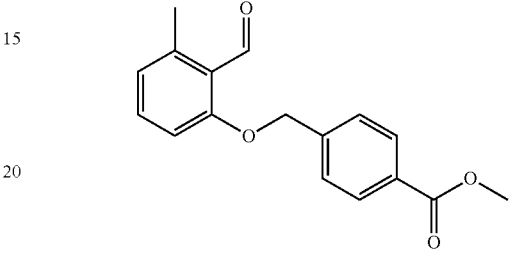

Potassium carbonate (35.81 g, 0.259 mol) was added to a solution of 2-hydroxy-6-methylbenzaldehyde (23.52 g, 0.173 mol), 4-(bromomethyl)benzoic acid methyl ester (39.57 g, 0.173 mol) and [18]-crown-6 (0.69 g, 2.6 mmol) in acetone (250 ml) and the mixture was heated for 24 h at 40° C. After cooling, the suspension was diluted with n-heptane (200 ml) and filtered. The filtrate was concentrated on a rotary evaporator. The brownish solid was dissolved in 1:2 n-heptane/dichloromethane (100 ml) and filtered over silica gel. The filtrate was concentrated on a rotary evaporator and 46.48 g (0.163 mol; 94%) of a yellowish solid was obtained.

$^1$H-NMR (CDCl$_3$, 400 MHz): δ=10.75 (s, 1H; HC=O), 8.06 (d, 2H; J=8.0 Hz, Ar—H), 7.49 (d, 2H; J=8.5 Hz, Ar—H), 7.35 (t, 1H; J=8.0 Hz; Ar—H), 6.84 (m, 2H; Ar—H), 5.20 (s, 2H; O—CH$_2$), 3.91 (s, 3H; O—CH$_3$), 2.58 (s, 3H; Ar—CH$_3$).

$^{13}$C-NMR (CDCl$_3$, 100.6 MHz): δ=191.8 (C=O), 166.5 (C=O), 161.8 (Ar—C), 142.1 (Ar—C), 141.2 (Ar—C), 134.3 (Ar—CH), 129.9 (Ar—CH), 129.8 (Ar—C), 126.7 (Ar—CH), 124.5 (Ar—CH), 123.4 (Ar—C), 110.2 (Ar—CH), 69.7 (O—CH$_2$), 52.1 (O—CH$_3$), 21.4 (CH$_3$).

4th Stage: 4-[(2-formyl-3-methylphenoxy)-methyl]-benzoic acid (FPBA)

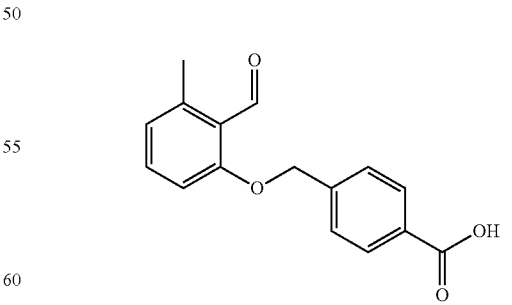

4-[(2-Formyl-3-methylphenoxy)-methyl]-benzoic acid methyl ester (46.38 g, 0.163 mol) was dissolved in dichloromethane (500 ml) and a solution of sodium hydroxide (19.58 g, 0.489 mol) in methanol (150 ml) was added to it. The reaction mixture was stirred at RT. After 24 h the suspension was filtered. The filtration residue was washed with dichloromethane (300 ml), suspended in water (300 ml) and hydrochloric acid (2N; 250 ml) was added to it. The suspension was stirred for 1 h at RT and filtered. The filtration residue was washed with water (500 ml) and dried. 41.89 g (0.155 mol; 95%) of a slightly yellowish solid was obtained.

$^1$H-NMR (acetone-d$_6$, 400 MHz): δ=10.74 (s, 1H; HC=O), 8.09 (d, 2H; J=8.1 Hz, Ar—H), 7.67 (d, 2H; J=8.2 Hz, Ar—H), 7.46 (t, 1H; J=8.2 Hz; Ar—H), 7.13 (d, 1H; J=8.4 Hz; Ar—H), 6.89 (d, 1H; J=8.0 Hz; Ar—H), 5.38 (s, 2H; O—CH$_2$), 2.53 (s, 3H; Ar—CH$_3$).

$^{13}$C-NMR (acetone-d$_6$, 100.6 MHz): δ=191.6 (C=O), 167.0 (C=O), 162.3 (Ar—C), 142.2 (Ar—CH), 141.5 (Ar—C), 134.8 (Ar—CH), 130.7 (Ar—CH), 130.2 (Ar—CH), 127.6 (Ar—CH), 124.6 (Ar—CH), 123.9 (Ar—C), 111.3 (Ar—CH), 70.0 (O—CH$_2$), 20.8 (CH$_3$).

5$^{th}$ Stage: 4-[(2-formyl-3-methylphenoxy)-methyl]-benzoic acid-(2-methacryloyloxyethyl)-ester (PEMA)

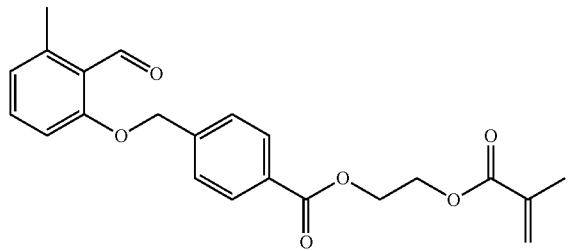 [SMILES: C=C(C)C(=O)OCCOC(=O)c1ccc(COc2cccc(C)c2C=O)cc1]

A mixture of 4-[(2-formyl-3-methylphenoxy)-methyl]-benzoic acid (43.77 g, 0.162 mol), hydroxyethyl methacrylate (21.07 g, 0.162 mol), N,N-dimethylaminopyridine (1.83 g, 15 mmol) and 2,6-di-tert-butyl-4-methylphenol (25 mg) in dichloromethane (500 ml) was cooled to 0° C. N,N'-Dicyclohexylcarbodiimide (36.75 g, 0.178 mol) was added in portions within 20 min. The reaction mixture was stirred for 2 h accompanied by ice cooling and then at room temperature. After 20 h the suspension was diluted with n-heptane (250 ml) and filtered over silica gel. The filtrate was concentrated on a rotary evaporator. The crude product was purified by means of column chromatography (SiO$_2$, n-heptane/ethyl acetate/dichloromethane 4:1:2; R$_f$=0.4). 49.98 g (0.130 mol; 81%) of a slightly yellowish solid was obtained.

$^1$H-NMR (CDCl$_3$, 400 MHz): δ=10.75 (s, 1H; HC=O), 8.07 (d, 2H; J=8.5 Hz, Ar—H), 7.51 (d, 2H; J=8.5 Hz, Ar—H), 7.36 (t, 1H; J=8.0 Hz; Ar—H), 6.85 (m, 2H; Ar—H), 6.15 (m, 1H; =CH), 5.59 (m, 1H; =CH), 5.22 (s, 2H; O—CH$_2$—Ar), 4.58 (m, 2H; O—CH$_2$—CH$_2$), 4.50 (m, 2H; O—CH$_2$—CH$_2$), 2.58 (s, 3H; Ar—CH$_3$), 1.95 (m, 3H; CH$_3$).

$^{13}$C-NMR (CDCl$_3$, 100.6 MHz): δ=191.8 (C=O), 167.0 (C=O), 165.8 (C=O), 161.7 (Ar—C), 142.1 (Ar—C), 141.5 (Ar—C), 135.8 (=C), 134.3 (Ar—CH), 130.0 (Ar—CH), 129.5 (Ar—C), 126.7 (Ar—CH), 126.0 (=CH$_2$), 124.6 (Ar—CH), 123.5 (Ar—C), 110.2 (Ar—CH), 69.7 (O—CH$_2$—Ar), 62.6 (O—CH$_2$—CH$_2$), 62.3 (O—CH$_2$—CH$_2$), 21.3 (Ar—CH$_3$), 18.2 (CH$_3$).

Example 2

2-Stage Photopolymerization of a PEMA-Containing Resin Mixture

Starting from the monomer PEMA from Example 1, with the comonomers butyl methacrylate (BMA) and methyl methacrylate (MMA) monomer mixtures were produced, to which in each case 50 mmol/l bis(2,4,6-trimethylbenzoyl)phenylphosphine oxide (Irgacure® 819, from Ivoclar) was added (Table 1). The mixtures were first irradiated with a blue LED (X=445-465 nm, intensity: 7/cm$^2$) for 1 h. Then the mixtures were irradiated with a UV-A radiation source (λ$_{max}$=350 nm) with an intensity of 5/cm$^2$, at a temperature of approximately 45° C., for different times in a photoreactor (LZC-4V model, Luzchem Research Inc., Ottawa, Canada). The mechanical properties (reduced elastic modulus E$_r$ and hardness) of the cured samples were determined by means of nanoindentation (instrumented penetration test) using a Hysitron TL950 nanoindenter (Bruker) (cf. Table 1). The load-controlled measurements with a Berkovich tip were carried out at a maximum loading force of 2000 μN with a loading time of 1 s, a loading segment of 2 s as well as an unloading of 1 s. The analysis was effected using the Oliver-Pharr method (W. C. Oliver, G. M. Pharr, J. Mater In: Res. 7, 1992, p. 1564). Measurement was performed using measurement methods analogous to B. Sandmann, B. Happ, J. Vitz, R. M. Paulus, M. D. Hager, P. Burtscher, N. Moszner, U. S. Schubert, Macromol. Chem. Phys. 2014, 215, 1603.

TABLE 1

Compositions (mol-%) of resins with BMA, MMA and PEMA and mechanical properties of the cured samples

| BMA$^a$ [%] | MMA$^b$ [%] | PEMA$^c$ [%] | t$_{cure}$ [min] | E$_r$ [GPa] | Hardness [MPa] |
|---|---|---|---|---|---|
| 30 | 55 | 15 | 0 | 2.97 ± 0.49 | 34.3 ± 3.9 |
| 30 | 55 | 15 | 1 | 4.58 ± 0.02 | 165.3 ± 1.8 |
| 30 | 55 | 15 | 2 | 5.1 ± 0.02 | 263.8 ± 3.6 |
| 30 | 55 | 15 | 5 | 5.27 ± 0.03 | 294.3 ± 5.7 |

$^a$= Butyl methacrylate
$^b$= Methyl methacrylate
$^c$= 4-[(2-Formyl-3-methylphenoxy)-methyl]-benzoic acid-(2-methacryloyloxyethyl)-ester (Ex. 1)

The results in Table 1 prove that the elastic modulus and the hardness of the test pieces increase with increasing UV-A irradiation, which is brought about by a dimerization of the photochemically induced o-quinodimethane building blocks. In comparison, the reference values for commercially obtainable dental braces made of polyurethane (Invisalign Aligner, from Align Technology BV) are E$_r$=0.95±0.09 GPa and 45±1.7 MPa.

Example 3

Simultaneous Photopolymerization of PEMA-Containing Resin Mixtures

Starting from the monomer PEMA from Example 1, with the comonomers BMA, MMA and/or methyl acrylate (MA) monomer mixtures were produced, to which 50 mmol/l bis(2,4,6-trimethylbenzoyl)phenylphosphine oxide (Irgacure® 819, from Ivoclar) was added (Table 2). The resins were irradiated with a UV-A radiation source (λ$_{max}$=350 nm) with an intensity of 5/cm$^{-2}$ at a temperature of from 45 to 50° C. in a photoreactor (model LZC-4V, Luzchem Research Inc., Ottawa, Canada). Mechanical properties (elastic modulus E$_r$ and hardness) of the cured samples were again determined by means of nanoindentation, as described in Example 2 (Table 2).

TABLE 2

Resin compositions (mol-%) and mechanical properties of the cured samples

| Sample | BMA[a] [%] | MMA[b] [%] | MA[c] [%] | PEMA[d] [%] | $t_c^e$ [min] | $E_r^f$ [GPa] | Hardness [MPa] |
|---|---|---|---|---|---|---|---|
| A | 34 | 61 | / | 5 | 60 | 3.85 ± 0.07 | 109.7 ± 1.7 |
| B | 32 | 58 | / | 10 | 60 | 5.43 ± 0.11 | 350 ± 19.8 |
| C | / | / | 97 | 3 | 30 | 0.29 ± 0.04 | 52.0 ± 11.9 |
| D | / | / | 96 | 4 | 30 | 0.89 ± 0.03 | 89.6 ± 7.4 |
| E | / | / | 95 | 5 | 30 | 1.26 ± 0.22 | 93.9 ± 17.7 |
| F | / | / | 90 | 10 | 30 | 5.76 ± 0.06 | 329.3 ± 1.7 |

[a] = Butyl methacrylate
[b] = Methyl methacrylate
[c] = Methyl acrylate
[d] = 4-[(2-Formyl-3-methylphenoxy)-methyl]-benzoic acid-(2-methacryloyloxyethyl)-ester (Ex. 1)
[e] = Curing time
[f] = Reduced elastic modulus The results prove that polymer networks with adjustable flexibility can be produced depending on the resin composition. The elastic modulus and the hardness of the samples increase with an increasing proportion of PEMA.

Example 4

Radical Polymerization and Dimerization of Photochemically Induced o-Quinodimethane Building Blocks The polymer network synthesis was effected in two stages: 1st=radical copolymerization of the photoenolizable monomer PEMA by means of a thermal initiator and 2nd=irradiation with UV-A light for the dimerization of photochemically induced o-quinodimethane building blocks. Monomer mixtures (Table 3) were produced first and to these were added in each case 50 ml toluene as solvent, 2 mol-% azobisisobutyronitrile (AIBN) as thermal initiator and 2 mol-% lauryl mercaptan as chain regulator. After degassing of the monomer solutions, these were polymerized at 65° C. (sample b: 75° C.), the polymers were precipitated from aqueous methanol (10% water) and dried under fine vacuum. The determination of the number-average molecular mass $M_n$ and of the polydispersity index (PDI) of the copolymers obtained was effected by means of gel permeation chromatography (GPC) using a PSS SECurity system (Polymer Standards Service GmbH, Mainz), while the glass transition temperatures $T_g$ were determined by means of differential scanning calorimetry (DSC) with the device Q100 SDC V9.6 Build 290 (TA Instruments) (Table 4). The DSC measurements were effected between −40 and 120° C. with a heating or cooling rate of 10° C./min. In each case two heating and cooling cycles were recorded, wherein the glass transition temperatures listed are taken from the second heating segment.

TABLE 3

Monomer compositions (mol-%) for the radical copolymerization

| Sample | BMA[a] [%] | mmol | MMA[b] [%] | mmol | PEMA[c] [%] | mmol | THFMA[d] [%] | mmol | IBOMA[e] [%] | mmol |
|---|---|---|---|---|---|---|---|---|---|---|
| A | — | — | 77 | 24.8 | 23 | 6.04 | — | — | — | — |
| B | 34 | 9.67 | 46 | 15.65 | 20 | 6.23 | — | — | — | — |
| C | 65 | 20.38 | 15 | 4.70 | 20 | 6.20 | — | — | — | — |
| D | — | — | — | — | 24 | 1.66 | 76 | 6.72 | — | — |
| E | — | — | — | — | 20 | 1.80 | — | — | 80 | 7.25 |

[a] = Butyl methacrylate
[b] = Methyl methacrylate
[c] = 4-[(2-Formyl-3-methylphenoxy)-methyl]-benzoic acid-(2-methacryloyloxyethyl)-ester
[d] = Tetrahydrofurfuryl methacrylate
[e] = Isobornyl methacrylate

TABLE 4

GPC and DSC results of the copolymers

| Sample | BMA[a] [%] | MMA[b] [%] | PEMA[c] [%] | THFMA[d] [%] | IBOMA[e] [%] | $t_p^f$ [h] | $M_n$ [g/mol$^{-1}$] | PDI | $T_g$ [° C.] |
|---|---|---|---|---|---|---|---|---|---|
| A | / | 77 | 23 | / | / | 24 | 6800 | 1.8 | 65 |
| B | 34 | 46 | 20 | / | / | 4 | 10,000 | 1.7 | 51 |
| C | 65 | 15 | 20 | / | / | 21 | 7000 | 1.7 | 23 |

TABLE 4-continued

GPC and DSC results of the copolymers

| Sample | BMA[a] [%] | MMA[b] [%] | PEMA[c] [%] | THFMA[d] [%] | IBOMA[e] [%] | $t_p^f$ [h] | $M_n$ [g/mol$^{-1}$] | PDI | $T_g$ [°C.] |
|---|---|---|---|---|---|---|---|---|---|
| D | / | / | 24 | 76 | / | 22 | 5700 | 1.9 | 40[g] |
| E | / | / | 20 | / | 80 | 22 | 6600 | 1.4 | 116[g] |

[a] = Butyl methacrylate
[b] = Methyl methacrylate
[c] = 4-[(2-Formyl-3-methylphenoxy)-methyl]-benzoic acid-(2-methacryloyloxyethyl)-ester (Ex. 1)
[d] = Tetrahydrofurfuryl methacrylate
[e] = Isobornyl methacrylate
[f] = $t_p$ = Polymerization time
[g] = Here the DSC measurements were carried out in the temperature range up to 140° C.

The results of the regulated copolymerizations yielded copolymers with a number-average molecular mass between 6800 and 10,000 g/mol and a glass transition temperature between 40 and 116° C. The copolymers A to E can be shaped at 140° C. Films and compacts were produced, which proved to be insoluble after irradiation with UV light (365 nm) for 2 min, which is brought about by a dimerization of the photochemically induced o-quinodimethane building blocks.

Example 5

Simultaneous Photopolymerization of o-Methylbenzaldehyde Methacrylates and MA-Containing Resin Mixtures With the monomer PEMA from Example 1 monomer mixtures with the comonomer MA (samples a-c) or MA and a liquid 2-ureido-4[1H]-pyrimidinone methacrylamide (UPyMAA, sample d), which was synthesized in accordance with the literature (Heinzmann et al., Macromolecules 48 (2015) 8128-8136), were produced and 2 mol-% bis(2,4,6-trimethylbenzoyl)phenylphosphine oxide (Irgacure® 819, from Ivoclar) were added (Table 5). The resins were irradiated with a UV-A radiation source ($\lambda_{max}$=350 nm) with an intensity of 5/cm$^{-2}$ in each case in aluminium dishes inside a photoreactor (model LZC-4V, Luzchem Research Inc. Ottawa, Canada). The temperature was room temperature (RT) or 50° C. The mechanical properties (elastic modulus and hardness) of the cured samples were again determined by means of nanoindentation, as described in Example 2 (Table 5).

TABLE 5

Composition (mol-%) of resins with PEMA and MA and mechanical properties of the cured samples

| Sample | UPyMAA[a] (%) | PEMA[b] (%) | MA[c] (%) | $T_c^d$ (°C.) | $t_c^e$ (min.) | $E_r$ (GPa) | Hardness (MPa) |
|---|---|---|---|---|---|---|---|
| A | / | 15 | 85 | 50 | 30 | 5.37 ± 0.32 | 328.2 ± 12.1 |
| B | / | 20 | 80 | 50 | 30 | 5.23 ± 0.04 | 301.9 ± 1.9 |
| C | / | 20 | 80 | 50 | 45 | 5.49 ± 0.03 | 303.2 ± 1.4 |
| D | 10 | 10 | 80 | 50 | 45 | 3.51 ± 0.01 | 123.5 ± 1.5 |

[a] = 2-Ureido-4[1H]-pyrimidinone methacrylamide
[b] = 4-[(2-Formyl-3-methylphenoxy)-methyl]-benzoic acid-(2-methacryloyloxyethyl)-ester
[c] = Methyl acrylate
[d] = Curing temperature
[e] = Curing time The results prove that polymer networks with very different hardness and elastic modulus can be produced with a changing proportion of crosslinker according to the invention (PEMA). The values obtained lie in a range which is typical for corrective splints.

The invention claimed is:

1. A method of manufacturing a medical-technical material for the production of medical devices, implants for auditory prostheses, cartilage or bone replacement parts, as a material for ophthalmology, or for the production of intraocular lenses comprising
stereolithographically processing a composition comprising
a) 0.1 to 50 wt.-% of at least one benzaldehyde derivative of Formula I,

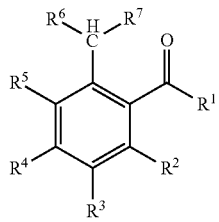

Formula I in which
R$^1$ is hydrogen, a branched or unbranched, saturated or unsaturated C$_1$-C$_{14}$ alkyl group which can be interrupted by O or S, a C$_6$-C$_{14}$ aryl group or a C$_4$-C$_{14}$ heteroaryl group which can contain N, O or S, wherein the alkyl, aryl or heteroaryl groups can be substituted with thioether, amino, alkoxy or alkyl groups with 1 to 14 carbon atoms or C$_6$-C$_{14}$ aryl groups and wherein the substituents can be bridged to each other,
R$^{2-5}$ in each case independently of each other are hydrogen, an NH$_2$ group, a branched or unbranched, saturated or unsaturated thioether, amino, alkoxy or alkyl group with 1 to 14 carbon atoms, a branched or unbranched, saturated or unsaturated $C_7$-$C_{15}$ arylalkoxy group, benzyloxy group (Ph-$CH_2$—O—), or a $C_6$-$C_{14}$ aryl group which can be bound via O or S, wherein $R^{2-3}$ can be bridged to each other and $R^2$ and/or $R^4$ is/are —X—SP-PG, X is dispensed with or is —O—, —CO—O— or —O—CO—, SP is a linear or branched $C_1$-$C_6$ alkylene group, wherein the alkylene group can be interrupted by O, S, —CO—O—, —O—CO— and/or phenylene, PG is a polymerizable group, $R^{6-7}$ in each case independently of each other are hydrogen or a $C_1$-$C_{10}$ alkyl group which can be branched or unbranched, saturated or unsaturated, b) 30 to 99 wt.-% of at least one further monofunctional radically or cationically polymerizable monomer, c) 0 to 20 wt.-% of at least one multifunctional radically or cationically polymerizable monomer, d) 0.001 to 5.0 wt.-% of at least one photoinitiator, e) 0 to 5.0 wt.-% additive(s), in each case relative to the total mass of the material, wherein said composition does neither contain further 1,3-dienes nor dienophiles, into the medical-technical material and curing the medical-technical material during or after the stereolithographically processing step, wherein the curing is effected in two stages, the first stage comprising irradiation of the material with visible light and the second stage irradiation of the material with UV-A light.

2. The method of manufacturing according to claim 1, wherein the variables of Formula I have the following meanings:

$R^1$ is hydrogen or $C_1$-$C_4$ alkyl group, $R^{2-5}$ in each case independently of each other are hydrogen or a $C_1$-$C_4$ alkoxy or $C_1$-$C_4$ alkyl group, wherein $R^2$ and/or $R^4$ is/are —X—SP-PG, X is —O—, SP is a linear $C_2$-$C_6$ alkylene group, wherein the alkylene group can be interrupted by O, —CO—O— and/or phenylene, $C_2$-$C_4$ alkylene group or —$CH_2$-Ph-CO—O—$CH_2CH_2$—, PG is a cationically or radically polymerizable group, a (meth)acrylate group or an acrylamide group, $R^{6-7}$ are both hydrogen or $R^6$=$C_1$-$C_{10}$ alkyl and $R^7$=H.

3. The method of manufacturing according to claim 1, wherein the variables of Formula I have the following meanings:

$R^1$ is hydrogen or —$CH_3$, $R^{2-3}$ in each case independently of each other are hydrogen, —$CH_3$ or —$OCH_3$, wherein $R^2$ or $R^4$ is —X—SP-PG, X is —O—, SP is a linear $C_2$-$C_6$ alkylene group, wherein the alkylene group can be interrupted by O, —CO—O— and/or phenylene, a $C_2$-$C_4$ alkylene group or —$CH_2$-Ph-CO—O—$CH_2CH_2$—, PG is a cationically or radically polymerizable group, a (meth)acrylate group or an acrylamide group, $R^{6-7}$ in each case are hydrogen.

4. The method of manufacturing according to claim 1, wherein the variables of Formula I have the following meanings:

$R^1$ is hydrogen, $R^{2-3}$ in each case independently of each other are hydrogen or —$CH_3$, wherein $R^2$ or $R^4$ is —X—SP-PG, X is —O—, SP is a linear $C_2$-$C_4$ alkylene group, wherein the alkylene group can be interrupted by O, —CO—O— and/or phenylene, a $C_2$ alkylene group or —$CH_2$-Ph-CO—O—$CH_2CH_2$—, PG is a radically polymerizable group, a (meth)acrylate group or an acrylamide group, $R^{6-7}$ in each case are hydrogen.

5. The method of manufacturing according to claim 1, in which PG is a radically polymerizable group, which is selected from a vinyl, (meth)acrylate or (meth)acrylamide group.

6. The method of manufacturing according to claim 1, in which PG is a cationically polymerizable group, which is selected from an epoxy, oxetane or vinyl ether group.

7. The method of manufacturing according to claim 1, wherein in the at least one polymerizable additional monomer is selected from methyl acrylate (MA), ethyl acrylate (EA), methyl methacrylate (MMA), butyl methacrylate (BMA), tetrahydrofurfuryl methacrylate (THEMA), isobornyl methacrylate (IBOMA) or a mixture thereof.

8. The method of manufacturing according to claim 1, wherein the photoinitiator (d) comprises at least one initiator for the polymerization by UV-A light and at least one initiator for the polymerization by visible light.

9. The method of manufacturing according to claim 1, wherein the composition additionally contains at least one inorganic filler.

10. A method of manufacturing or repairing extraorally dental braces, corrective splints or templates for correcting malocclusions comprising stereolithographically processing a composition comprising a) 0.1 to 50 wt.-% of at least one benzaldehyde derivative of Formula I,

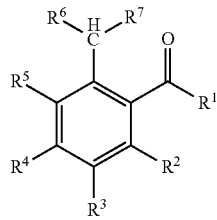

Formula I in which $R^1$ is hydrogen, a branched or unbranched, saturated or unsaturated $C_1$-$C_{14}$ alkyl group which can be interrupted by O or S, a $C_6$-$C_{14}$ aryl group or a $C_4$-$C_{14}$ heteroaryl group which can contain N, O or S, wherein the alkyl, aryl or heteroaryl groups can be substituted with thioether, amino, alkoxy or alkyl groups with 1 to 14 carbon atoms or $C_6$-$C_{14}$ aryl groups and wherein the substituents can be bridged to each other, $R^{2-5}$ in each case independently of each other are hydrogen, an $NH_2$ group, a branched or unbranched, saturated or unsaturated thioether, amino, alkoxy or alkyl group with 1 to 14 carbon atoms, a branched or unbranched, saturated or unsaturated $C_7$-$C_{15}$ arylalkoxy group, benzyloxy group (Ph-$CH_2$—O—), or a $C_6$-$C_{14}$ aryl group which can be bound via O or S, wherein $R^{2-5}$ can be bridged to each other and $R^2$ and/or $R^4$ is/are —X—SP-PG, X is dispensed with or is —O—, —CO—O— or —O—CO—, SP is a linear or branched $C_1$-$C_6$ alkylene group, wherein the alkylene group can be interrupted by O, S, —CO—O—, —O—CO— and/or phenylene, PG is a polymerizable group, $R^{6-7}$ in each case independently of each other are hydrogen or a $C_1$-$C_{10}$ alkyl group which can be branched or unbranched, saturated or unsaturated, b) 30 to 99 wt.-% of at least one further monofunctional radically or cationically polymerizable monomer, c) 0 to 20 wt.-% of at least one multifunctional radically or cationically polymerizable monomer, d) 0.001 to 5.0 wt.-% of at least one initiator, in particular photoinitiator, e) 0 to 5.0 wt.-% additive(s), in each case relative to the total mass of the material, wherein said composition does neither contain further 1,3-dienes nor dienophiles, into a medical device, implant for auditory prostheses, cartilage or bone replacement part, or an intraocular lens, and curing the medical device, implant for auditory prostheses, cartilage or bone replacement part, or intraocular lens during or after the stereolithographic processing step, wherein the curing is effected in two stages, the first stage comprising ir-radiation of the material with visible light and the second stage irradiation of the material with UV-A light.

11. The method according to claim 1, wherein the composition comprises a) 1 to 40 wt.-% of at least one benzaldehyde derivative of Formula I, b) 40 to 95 wt.-% of at least one further monofunctional radically or cationically polymerizable monomer, c) 0 to 15 wt.-% of at least one multifunctional radically or cationically polymerizable monomer, d) 0.01 to 3.0 wt.-% of at least one initiator or photoinitiator, e) 0 to 3.0 wt.-% additive(s), in each case relative to the total mass of the material.

12. The method according to claim 1, wherein the composition comprises a) 1 to 20 wt.-% of at least one benzaldehyde derivative of Formula I, b) 50 to 95 wt.-% of at least one further monofunctional radically or cationically polymerizable monomer, c) 0 to 10 wt.-% of at least one multifunctional radically or cationically polymerizable monomer, d) 0.1 to 1.0 wt.-% of at least one initiator or photoinitiator, e) 0 to 1.5 wt.-% additive(s), in each case relative to the total mass of the material.

13. The method according to claim 1, wherein the at least one additional polymerizable monomer is a monofunctional acrylate or methacrylate and wherein the at least one additional polymerizable monomer (c) is a multifunctional acrylate or methacrylate.

* * * * *